United States Patent [19]

Guillaume et al.

[11] Patent Number: 4,584,841

[45] Date of Patent: Apr. 29, 1986

[54] ARTIFICIAL HIBERNATOR AND PROCESS FOR COLD PRESERVATION OF A HUMAN BEING OR ANIMAL IN A PREDETERMINED POSITION

[76] Inventors: Gerard Guillaume; Lola Guillaume nee Henry, both of 33, 35, rue Rennequin, 75017 Paris, France

[21] Appl. No.: 619,221

[22] Filed: Jun. 11, 1984

[30] Foreign Application Priority Data

Jun. 30, 1983 [FR] France .............................. 83 10836

[51] Int. Cl.⁴ ............................................ F25D 25/00
[52] U.S. Cl. .......................................... 62/62; 27/11; 62/100; 62/268; 62/452; 62/457
[58] Field of Search ............... 27/1, 2, 11; 62/446, 62/451, 452, 457, 268, 62, 100

[56] References Cited

U.S. PATENT DOCUMENTS

| | | | |
|---|---|---|---|
| 1,887,665 | 11/1932 | Truman | 27/11 |
| 2,959,938 | 11/1960 | Giandini | 62/457 |
| 3,257,820 | 6/1966 | Case et al. | 27/11 |
| 3,408,711 | 11/1968 | Pauliukonis | 27/11 |
| 3,488,818 | 1/1970 | Orr | 27/2 |
| 3,618,336 | 11/1971 | Palma | 62/457 |

*Primary Examiner*—Ronald C. Capossela
*Attorney, Agent, or Firm*—Browdy and Neimark

[57] ABSTRACT

The invention relates to a hibernator suitable for keeping under permanent refrigeration a cadaver placed in a desired position and constantly visible from the outside. The hibernator consists essentially of a structure whose refrigerated and fluid-tight upper part (1) serves as a resting place for the being to be preserved, with at least a double-glazed wall; and whose lower part (2) or base is intended to house the refrigerating unit (3) and various technical elements including pipes (22 to 24) to assure partial vacuum in determined sectors of the structure of the resting place. Also disclosed is a process for preservation and showing of cadavers which have previously been frozen or imprisoned in blocks of translucid ice.

20 Claims, 6 Drawing Figures

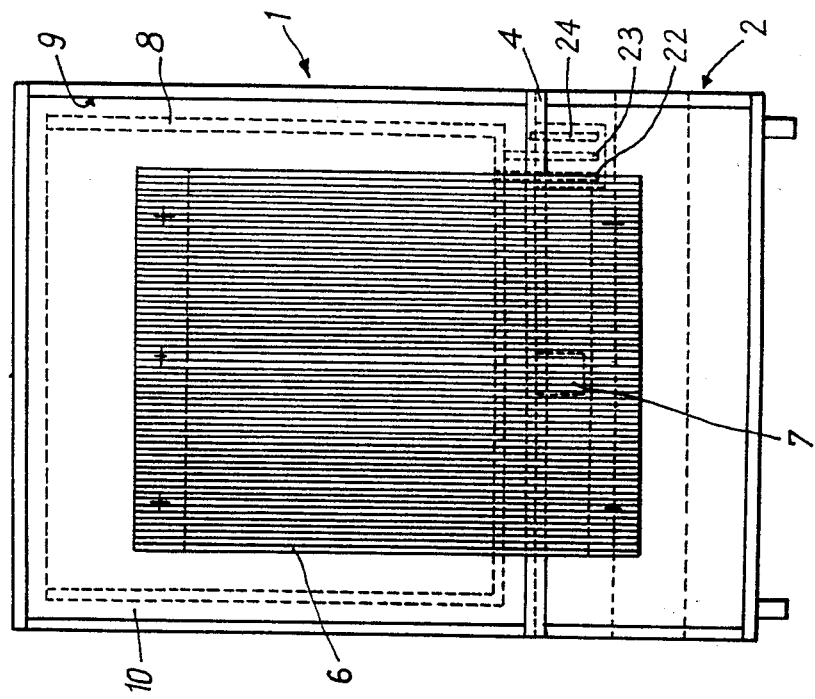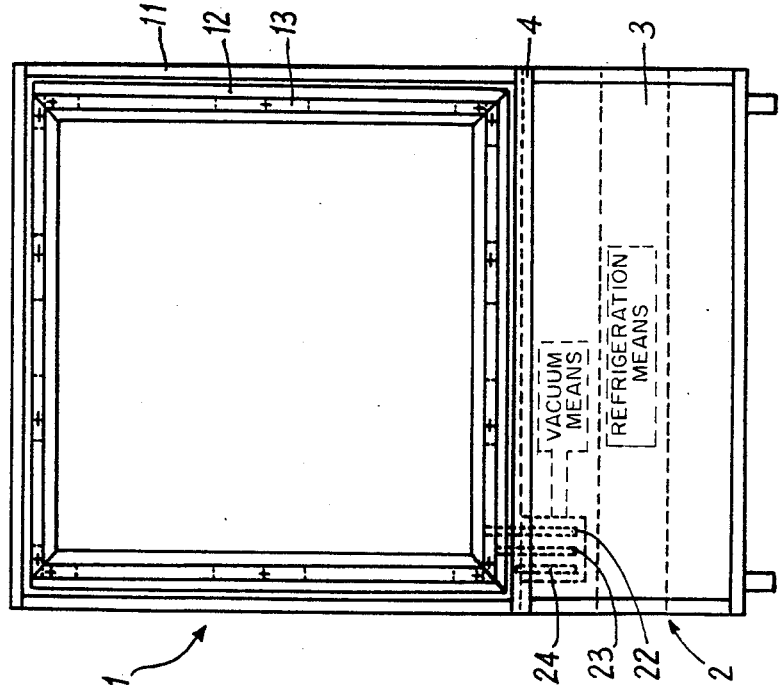

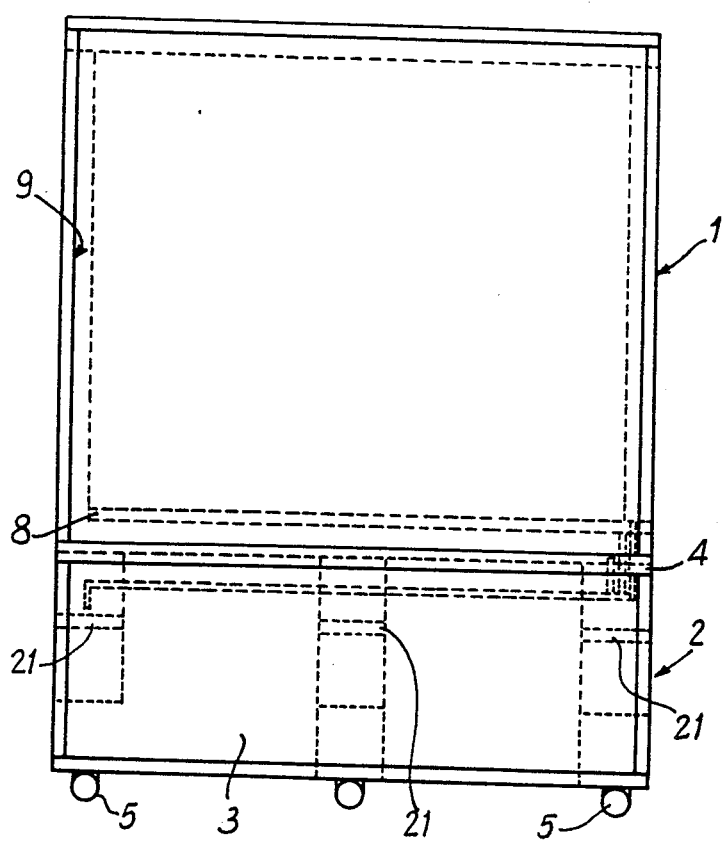
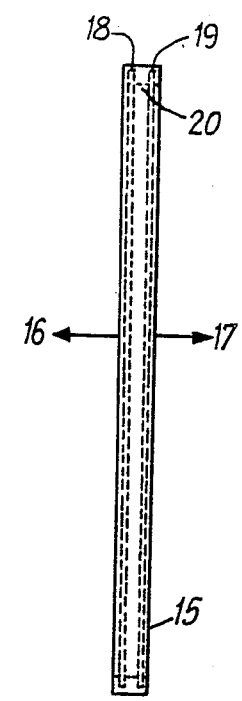
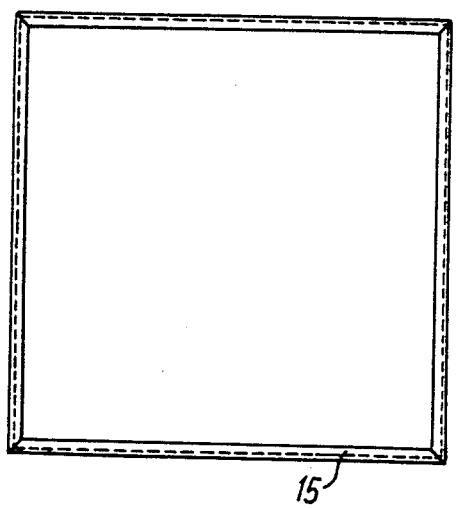
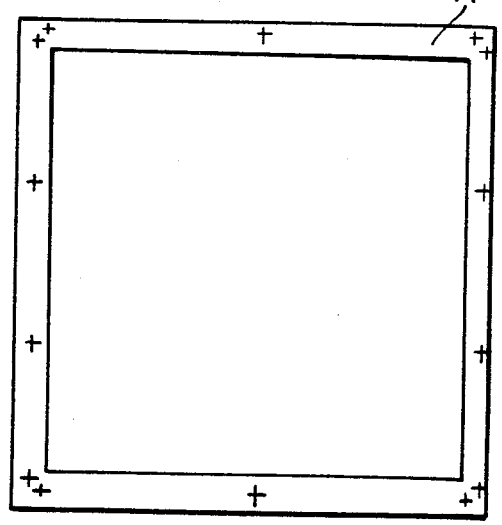

ARTIFICIAL HIBERNATOR AND PROCESS FOR COLD PRESERVATION OF A HUMAN BEING OR ANIMAL IN A PREDETERMINED POSITION

BACKGROUND OF THE INVENTION

This invention relates to the preservation by cold of human beings or animals. It relates more particularly to a hibernator especially suited to keeping under permanent refrigeration a cadaver placed in a predetermined position and visible from the outside.

Numerous processes and devices have already been described and used for preserving organs under hypothermia and for storing refrigerated foods and meats. Various systems have also been recommended making it possible to cool mortuary tables of human beings and coffinlike containers intended to be shipped to successive places and/or stored for a predetermined period before final burial.

However, until now there apparently has been no concern about the problem of showing a cadaver and permanently preserving it in a public or private place. For example, it might be desired to have near or in the context of its environment during life an animal that was particularly dear and which it would be desirable to view permanently in a preferred position or attitude.

OBJECTS AND SUMMARY OF THE INVENTION

One of the purposes of the invention is to provide a solution to this problem of preservation and showing of a dead being in a predetermined position.

Another purpose is to assure that the individual or animal looks natural without resorting to standard means of stuffing or clinical and/or chemical treatments.

To achieve these and other purposes, there is provided a mobile refrigerated apparatus especially adapted to preserving a cadaver for a long period of time. In addition, the invention comprises a process of artificial hibernation of a cadaver adapted for implementation as soon as the being dies.

According to its most general characteristics, the novel artificial hibernator according to the invention essentially comprises: (a) a multiple-wall outer structure including two separate but integral compartments including an upper rigorously fluid-tight cell, in relation to the outside, and a lower cell containing the elements of a refrigerating unit, at least one of the walls of this structure being transparent; (b) an inside box placed in the upper cell, acting as the resting place for the refrigerated being and separated from the walls of the latter by a thermally insulating means; (c) a door having a porthole provided with two panes between which a vacuum prevails and comprising a shaped seal able to assure a rigorous fluid-tightness between the door and frame of the structure; (d) pipes placed in the lower cell and intended to assure a partial vacuum in the resting place and porthole.

BRIEF DESCRIPTION OF THE DRAWINGS

For a better understanding of these characteristics and the various secondary elements and variant embodiments, a nonlimiting example of embodiment is described below, and is illustrated by the accompanying drawings showing a cold preservation apparatus in which:

FIG. 1 illustrates a front view of the apparatus showing the general construction of the structure;

FIG. 2 illustrates a rear view of the apparatus on which is mounted the system for evacuation of the heat from the condenser of the refrigerating unit;

FIG. 3 shows a side view of the apparatus;

FIG. 4 show a closing panel of the glazed door;

FIGS. 5 and 6 illustrate plan, and cross sectional, views, respectively, of the frame and glass walls of the door.

DETAILED DESCRIPTION OF THE INVENTION

As shown in the drawings, an artificial hibernator according to the invention comprises an upper or main compartment 1 serving as a fluid-tight refrigerated container and a lower compartment 2 provided with spaces 3 for housing a refrigerating means in the nature of a freezer unit and various pipes. The two compartments 1 and 2 are separated but solidly affixed by the T-shaped member 4. The apparatus is made mobile by installation of self locking wheels 5 under the structure (see FIG. 3). The back face of the apparatus, which can be seen in FIG. 2, supports heat evacuation panel 6 and a thermostat positioned as shown at 7.

In compartment 1 there is installed box 8 serving as a partition for the evaporator, the latter being insulated from inside wall 9 of the upper compartment by a plastic foam installed in surrounding space 10 as, for example, a polyurethane foam with a resistance greater than 2 kg/cm$^2$ (type ECCOFOAM FPH of Grace & Co., or equivalent material). According to one variation of the invention, the insulating material in this surrounding space 10 can be replaced by apparatus for generating suction or vacuum (by means of pipes) which will be explained below.

Referring again to FIG. 1, the upper compartment of the structure comprises on at least three side faces a triple layer wall comprising:

(1) an outside trim angle member 11,
(2) an inside reinforcing angle member 12, and
(3) a U-shape member 13 on which rests the closing panel 14 (seen in FIG. 4) of the glazed door which fits on the front face of compartment 1 by a frame 15 (shown in FIG. 5).

The glazed door is advantageously provided, as can be seen in FIG. 6, with a double-pane frame, having an inside 16, an outside 17, a glass 18 which is preferably 5–6 mm thick, and a triplex glass 19 on the same order of thickness. A vacuum is created between the two glass walls when the animal (or other being) is put into the hibernator. On the inside of frame 15 is provided a contoured seal 20, for example, of the neoprene rubber type, making it possible to achieve a perfect fluid-tightness between the door closing panel 14 and the cooperating wall of the frame 15.

The lower compartment 2 of the structure is provided with reinforcing beams 21, as well as the refrigerating unit and various pipes intended particularly for providing a vacuum in various parts of the apparatus. For example, a pipe 22 is provided for creating the vacuum between glass walls 18 and 19; a pipe 23 for partial aspiration in the frame to prevent the appearance of moisture and, optionally, a pipe 24 when it is desired to create a vacuum between box 8 and wall 9 instead of installing a thermally insulating material.

In practice, the various constitutive parts of the apparatus are metal, except, of course, the glazed areas, and advantageously angle members and panels are of polished or anodized aluminum or various aluminum alloys. Of course, the embodiment described above is only an illustrative example, and several glazed panels can be provided instead of a single door, or metal panels having portholes can be used or, according to yet another variant, a semicircular shape of the hibernator can be used comprising a single curved multiglazed panel.

The invention also has as its object a process for using an apparatus of the above or equivalent type for cold preservation of a cadaver of a human being or, as described below, of an animal.

According to this process, as soon as the animal dies and when it can still be a manipulated, it is put in the preferred position for the desired viewing. The being can be subjected to various treatments, for example, by perfusion of preservative chemical compositions and/or injection into the eyes of polymerizable monomers or copolymers and/or hair lacquering or also coating with a fine plastic film; however, tests conducted so far by the applicant have shown that an apparently lasting preservation can be obtained in the absence of any treatment.

The animal is then introduced into an accessory freezer, kept at a temperature of −30 to −40° C. then, after obtaining perfect rapidity in the predetermined position, it is placed, as is, in box 8 of the hibernator where it is sufficient to keep the temperature at −5 to −23° C., on an average of −10 to −15° C., to obtain perfect preservation.

According to a variant embodiment, the animal is frozen in a block of ice of suitable shape, taking care to assure setting of the ice in successive stages, with a gradual variation of the temperature gradients to avoid any splitting or cracking of the final block. It is thus possible, in a way known in the art, to incorporate suitable chemical products in the ice water, making it possible to improve the transparency and limpidity of the final block. The block, imprisoning the animal, is then placed in the hibernator box.

As a result of the invention, it is possible to preserve a dear one as well as to store and show a cadaver, for example of animals, perfectly preserved, for scientific, technical or cultural purposes.

What is claimed is:

1. An artificial hibernator for cold preservation of cadavers of human beings and animals, characterized in that it essentially consists of:
    an outside multiple wall structure comprising two separate yet integral compartments including an upper fluid-tight compartment and a lower compartment enclosing a freezer unit, at least one of the walls of the structure being transparent;
    an internal box having box walls, said box being placed in the upper compartment, serving as a resting place for the being to be frozen and separated from the box walls by thermally insulating means;
    a door having a porthole provided with two panes between which a vacuum prevails and comprising a shaped seal able to assure fluid tightness between the door and said outside multiple wall structure;
    and means in the lower compartment for assuring a partial vacuum at least in the resting place and the porthole.

2. The hibernator according to claim 1, wherein the outside multiple wall structure comprises, at the upper compartment, several metal angle members asembled together, at least one of which acts as a reinforcement for the closing panel of the glazed porthole.

3. The hibernator according to claim 1, wherein said insulating means consists of a thermoplastic foam supporting at least 2 kg/cm$^2$.

4. The hibernator according to claim 2, wherein said insulating means consists of a thermoplastic foam supporting at least 2 kg/cm$^2$.

5. The hibernator according to claim 1, wherein said insulating means comprises a vacuum created in the space between the box and inside wall of the structure.

6. The hibernator according to claim 2, wherein said insulating means comprises a vacuum created in the space between the box and inside wall of the structure.

7. The hibernator according to claim 1, wherein the structure comprises, at the upper compartment, four panels including a rear panel, two side panels, and a front door provided with said glazed porthole; the side panels having a triple wall.

8. The hibernator according to claim 2, wherein the structure comprises, at the upper compartment, four panels including a rear panel, two side panels, and a front door provided with said glazed porthole, the side panels having a triple wall.

9. The hibernator according to claim 3, wherein the structure comprises, at the upper compartment, four panels including a rear panel, two side panels, and a front door provided with said glazed porthole, the side panels having a triple wall.

10. The hibernator according to claim 4, wherein the structure comprises, at the upper compartment, four panels including a rear panel, two side panels, and a front door provided with said glazed porthole, the side panels having a triple wall.

11. The hibernator according to claim 5, wherein the structure comprises, at the upper compartment, four panels including a rear panel, two side panels, and a front door provided with said glazed porthole, the side panels having a triple wall.

12. The hibernator according to claim 6, wherein the structure comprises, at the upper compartment, four panels including a rear panel, two side panels, and a front door provided with said glazed porthole, the side panels having a triple wall.

13. A hibernator according to claim 7, wherein three of said panels, excluding the rear panel, constitute a single unit semispherical in shape and provided with glazed multiple walls.

14. A hibernator according to claim 9, wherein three of said panels, excluding the rear panel, constitute a single unit semispherical in shape and provided with glazed multiple walls.

15. A hibernator according to claim 11, wherein three of said panels, excluding the rear panel, constitute a single unit semispherical in shape and provided with glazed multiple walls.

16. A process for cold preservation of the cadaver of a human being or animal, comprising:
    placing the cadaver in a desired final position; freezing said cadaver in a freezer at −30° to −40° C.;
    placing the frozen cadaver in a box of an artificial hibernator, comprising an outside multiple wall structure comprising two separate yet integral compartments including an upper fluid-tight compartment and a lower compartment enclosing a freezer unit, at least one of the walls of the structure being transparent; an internal box having box walls, said box being placed in the upper compartment, serving as a resting place for the being to be frozen and separated from the box walls by thermally insulating means; a door having a porthole provided with two panes between which a vacuum prevails and comprising a shaped seal able to assure fluid tightness between the door and said outside muliple wall structure; and means in the lower compartment for assuring a partial vacuum at least in the resting place and the porthole;

maintaining, in the box, the temperature between $-5°$ and $-25°$ C. and a slight vacuum.

17. The process according to claim 16, wherein during freezing, the cadaver is imprisoned in a block of ice of suitable shape, which is placed and kept permanently in said box.

18. A process according to claim 16, wherein said artificial hibernator into which said frozen cadaver is placed, is characterized in that said insulating means consists of a thermoplastic foam supporting at least 2 kg/cm$^2$.

19. A process according to claim 16, wherein said artificial hibernator into which said frozen cadaver is placed, is further characterized in that said insulating means comprises a vacuum created in the space between the box and inside wall of the structure.

20. A process according to claim 16, wherein said artificial hibernator into which said frozen cadaver is placed, is further characterized in that the structure comprises at the upper compartment, four panels including a rear panel, two side panels, and a front door provided with said glazed porthole; the side panels having a triple wall.

* * * * *